United States Patent
Sebillotte-Arnaud et al.

(10) Patent No.: US 6,579,907 B1
(45) Date of Patent: *Jun. 17, 2003

(54) FOAMING OIL-IN-WATER EMULSION BASED ON NONIONIC SURFACTANTS, A FATTY PHASE AND A CROSSLINKED CATIONIC OR ANIONIC POLYMER, AND ITS USE IN TOPICAL APPLICATIONS

(75) Inventors: Laurence Sebillotte-Arnaud, Creteil (FR); Emmanuelle Ambrosini, Paris (FR); Pascal Arnaud, Creteil (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,491

(22) Filed: Feb. 11, 2000

Related U.S. Application Data

(63) Continuation of application No. 09/187,036, filed on Nov. 6, 1998, now Pat. No. 6,162,834, which is a continuation of application No. 08/636,555, filed on Apr. 23, 1996, now abandoned.

(30) Foreign Application Priority Data

Apr. 25, 1995 (FR) .............................................. 95 04924

(51) Int. Cl.$^7$ ........................ A61K 47/32; A61K 47/00; A61K 47/30; A61K 6/00; A61K 7/00
(52) U.S. Cl. ............................... 514/772.4; 514/772.1; 514/772.3; 514/772.5; 514/777; 514/778; 514/781; 424/401; 424/47
(58) Field of Search ................ 424/47, 401; 514/772.3, 514/772.4, 772.1, 772.5, 777, 778, 781

(56) References Cited

U.S. PATENT DOCUMENTS

| | | | |
|---|---|---|---|
| 5,011,681 A | * | 4/1991 | Ciotti et al. |
| 5,429,815 A | * | 7/1995 | Faryniarz et al. |
| 5,531,993 A | * | 7/1996 | Griat |

FOREIGN PATENT DOCUMENTS

| | | |
|---|---|---|
| EP | 0617954 | 10/1994 |
| EP | 0642781 | 3/1995 |
| FR | 2720934 | 12/1995 |
| WO | WO 9207543 | 5/1992 |
| WO | WO 9503781 | 2/1995 |

OTHER PUBLICATIONS

English language Derwent Abstract of FR 2720934.
English language Derwent Abstract of EP 642781.
English language Derwent Abstract of EP 617954.
English language Derwent Abstract of WO 920753.
Hansen, "The Three Dimensional Solubility Parameter—Key to Pain Component Affinities: I Solvents, Plasticizers, Polymers, and Resins," J. of Paint Technology, 39(504):104–117 (1967).

* cited by examiner

Primary Examiner—Sreeni Padmanabhan
Assistant Examiner—S. Jiang
(74) Attorney, Agent, or Firm—Finnegan, Henderson, Farrowbow, Garrett & Dunner LLP

(57) ABSTRACT

A forming oil-in-water emulsion in the form of a cream comprising, in an aqueous medium, at least:

a) from 5 to 20% of an exclusively nonionic surfactant system comprising at least one foaming nonionic surfactant;

b) from 10 to 50% of an oily phase containing at least one water-insoluble oil whose solubility parameters dD, dP and dH according to Hansen's solubility space satisfy the conditions:

$$15.5\ (J/cm^3)^{1/2} \leq dD \leq 18.0\ (J/cm^3)^{1/2}$$

and $$0\ (J/cm^3)^{1/2} \leq dA \leq 6.5\ (J/cm^3)^{1/2}$$

with $$dA=(dP^2+dH^2)^{1/2}$$

c) and, as a gelling agent, at least one crosslinked homopolymer or copolymer formed from at least one cationic or anionic monomer containing ethylenic unsaturation and from a crosslinking agent containing polyethylenic unsaturation. This composition is useful in cosmetics, dermatology and hygiene as a base for cleansing products for the skin, the hair, the mucous membranes and the scalp.

24 Claims, No Drawings

FOAMING OIL-IN-WATER EMULSION BASED ON NONIONIC SURFACTANTS, A FATTY PHASE AND A CROSSLINKED CATIONIC OR ANIONIC POLYMER, AND ITS USE IN TOPICAL APPLICATIONS

This is a continuation of application Ser. No. 09/187,036, filed Nov. 6, 1988, now U.S. Pat. No. 6,162,834, which is a continuation of application Ser. No. 08/636,555 filed Apr. 23, 1996 abandoned, which are incorporated herein by reference.

The present invention relates to forming oil-in-water emulsions in the form of a cream which are based on nonionic surfactants, a specific fatty phase and a crosslinked polymer comprising a cationic or anionic monomer containing ethylenic unsaturation. The present invention also relates to the use, in topical application, in particular in cosmetics and dermatology, of the disclosed foaming oil-in-water emulsions.

Foaming creams for cleansing the skin, which have a smooth feel, are generally in the form of an oil-in-water emulsion containing detergent surfactants and foaming agents. The oily phase makes it possible to soften the skin after rinsing. However, the oily phase has a tendency to inhibit the foaming properties of these formulations; it is said to "break" the foam. Consequently, the oily phase is introduced into foaming creams at low concentrations, generally of less than 5% by weight.

The surfactant systems used in foaming creams generally consist mainly of anionic surfactants. Despite their high foaming power and their good detergency, anionic surfactants have a certain irritant potential with regard to the skin and the eyes, and are incompatible with a large number of gelling agents.

In order to reduce this irritant potential, amphoteric surfactants and/or nonionic surfactants are combined with the anionic surfactants. In this regard, International patent application WO 93/02411 describes cleansing foaming compositions containing a surfactant system consisting of anionic surfactants combined with amphoteric surfactants in the presence of a water-insoluble oil and/or a wax.

A main object of the present invention is to be able to produce foaming creams based on an exclusively nonionic foaming surfactant system which may contain large amounts of oil without, however, jeopardizing the foaming power.

The prior art teaches that when compositions based on nonionic surfactants and oil are prepared, the foaming power of these compositions decreases when the proportion of oil is increased, relative to the surfactant system.

Such a teaching is illustrated, in particular, by European patent EP-617,954, which describes foaming cosmetic compositions comprising at least one nonionic surfactant of alkylpolyglucoside and/or polyglycerolated type and at least one crosslinked copolymer of maleic anhydride/alkyl vinyl ether and optionally an oil in very low proportions. This European patent document, however, does not describe foaming creams.

European patent EP-642,781 illustrates another aspect of this same principle by describing acidic non-foaming creams in the form of stable oil-in-water emulsions comprising a nonionic surfactant system, large amounts of oil and, as a stabilizer, crosslinked acrylamide/2-acrylamidopropanesulphonic acid copolymers. The compositions described in this patent are non-foaming.

Cosmetic compositions for cleansing the skin are moreover known from U.S. Pat. No. 5,011,681. These compositions are in the form of oil-in-water emulsions comprising a surfactant with an HLB of greater than or equal to 10, an oily phase comprising a poly(alpha-olefin) and a carboxylic copolymer containing from 95.9 to 98.8% by weight of a monoolefinically unsaturated monomer chosen from acrylic, methacrylic and ethacrylic acids, and from 1 to 3.5% of an arylic, methacrylic or ethacrylic acid ester with a $C_{10}$–$C_{30}$ alcohol. These compositions have the drawback of having a sticky feel, a runny appearance and elastic behavior. In addition, the foaming power of these compositions is insufficient. The compositions according to the present invention overcome these drawbacks of the prior art.

The Inventors have discovered, surprisingly, that the goal which they had set could be achieved by novel aqueous foaming compositions, in cream form, containing an exclusively nonionic surfactant system, a fatty phase having specific properties which will be defined below, it being possible for this fatty phase to be present in a large amount relative to the surfactant system, and a crosslinked polymer or copolymer of a cationic or anionic monomer containing ethylenic unsaturation.

The foaming creams in accordance with the invention are stable upon storage, have excellent foaming properties, are of better tolerance and harmlessness with respect to the skin and the eyes, i.e., are less irritating, when compared with the known foaming compositions and have good cosmetic properties when handled and to the touch.

In addition, the compositions of the invention may contain large amounts of oils which may be up to 6 to 10 times the amount of nonionic surfactants present in the formulation, without significantly affecting the foaming power or the stability of the compositions.

It is thus possible to introduce large amounts of care oil, i.e., any oil generally useful in the care of the skin and/or the hair, into such compositions and to obtain "two-in-one" foaming products.

The compositions according to the invention comprise, in a cosmetically acceptable aqueous medium, at least:

(a) from 5 to 20% by weight, relative to the total weight of the composition, of an exclusively nonionic surfactant system comprising at least one foaming nonionic surfactant;

(b) from 10 to 50% by weight, relative to the total weight of the composition, of an oily phase comprising at least one water-insoluble oil, wherein said at least one water-insoluble oil has solubility parameters dD, dP and dH according to Hansen's solubility space which satisfy the following conditions:

$$15.5 \ (J/cm^3)^{1/2} \leq dD \leq 18.0 \ (J/cm^3)^{1/2}$$

and $$0 \ (J/cm^3)^{1/2} \leq dA \leq 6.5 \ (J/cm^3)^{1/2}$$

with $$dA = (dP^2 + dH^2)^{1/2};$$

and (c) as a gelling agent, at least one crosslinked homopolymer or copolymer formed from at least one cationic or anionic monomer containing ethylenic unsaturation and from a crosslinking agent containing polyethylenic unsaturation; wherein said crosslinked copolymer does not comprise a copolymer containing a majority fraction of at least one olefinically unsaturated $C_3$–$C_6$ acid and a minority fraction of at least one ester of an olefinically unsaturated $C_3$–$C_6$ acid with a $C_{10}$–$C_{30}$ alcohol.

The compositions according to the invention preferably comprise, in a cosmetically acceptable aqueous medium:

(a) from 5 to 10% by weight, relative to the total weight of the composition, of an exclusively nonionic surfactant system comprising at least one foaming nonionic surfactant; and (b) from 10 to 30% by weight, relative to the total weight of the composition, of an oily phase comprising at least one water-insoluble oil whose solubility parameters are as defined above.

The foaming nonionic surfactants used according to the present invention are preferably chosen from nonionic surfactants having a foaming power preferably characterized by a foam height of more than 100 mm, more preferably characterized by a foam height of more than 120 mm, measured according to the Ross-Miles method for a 0.1% by weight solution of surfactant in distilled water at 25° C.

The foaming nonionic surfactants used in the compositions according to the invention are more preferably chosen from:

(i) the compounds of formula (I):

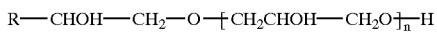
(I)

in which:

R represents aliphatic, cycloaliphatic or arylaliphatic radical or a mixture of radicals from 7 to 21 carbon atoms, it being possible for the aliphatic chains to be saturated or unsaturated, linear or branched and to contain sulphur or oxygen atoms, in particular ether, thioether or hydroxymethylene groups;

n is any integer or fraction greater than 1 and less than or equal to 10 and denotes the average degree of polymerization;

(ii) the compounds of formula (II)

in which $R^1$ is a monovalent hydrocarbon chain containing from 1 to 30 carbon atoms, G is a saccharide derivative containing from 5 to 6 carbon atoms and p is a statistical average value ranging and 1 to 6; and (iii) mixture thereof.

The compounds of formula (I) are described in French Patent No. FR 2,091,516, the disclosure of which is incorporated specifically by reference herein. Compounds of formula (I) are obtained by polycondensation of an α-diol containing a fatty chain onto the glycidyol.

Preferred compounds of formula (I) are those in which R represents an alkyl radical or a mixture of alkyl radicals containing from 9 to 12 atoms and n represents an average statictical value ranging from 3 to 4.

Dodecanediol polyglycerolated with 3.5 mol of glycerol, sold under the name CHIMEXANE NF by the company Chimex, is particularly used.

The compounds of formula (II) are described, in particular, in International patent application WO 94/27562, the disclosure of which is specifically incorporated by reference herein. The preferred compounds are those for which the radical $R^1$ is a $C_8$–$C_{16}$ alkyl radical, and even more preferred are those compounds whose degree of polymerization is equal to 1.4 or 1.6.

Examples of the compounds of formula (II) which may be mentioned are:

the alkylpolyglycosides marketed by Henkel under the names APG 225, APG 425 and APG 625;

the alkylpolyglucosides marketed by Henkel under the name GLUCOPON, similar to APG 625, but with a different degree of polymerization;

the alkylpolyglycosides marketed by Henkel under the name PLANTAREN, such as PLANTAREN 2000, which is a $C_8$–$C_{16}$-alkylpolyglucoside with a degree of polymerization of 1.4; PLANTAREN 1200, which is a $C_{12}$–$C_{18}$-alkylpolyglucoside with a degree of polymerization of 1.4; and PLANTAREN 1300, which is a $C_{12}$–$C_{18}$-alkylpolyglycoside with a degree of polymerization of 1.6.

The compositions according to the invention may also contain foaming silicone nonionic surfactants such as the polydimethylsiloxanes containing a polyoloside group, for instance SLM SPG 120 from the company Wacker or the polydimethylsiloxane derivatives containing alkylphosphobetaine groups, such as PECOSIL SPB-1240 from the company UCIB.

The definition of the solvents in the three-dimensional solubility space according to Hansen is described in the article by C. M. Hansen: "The three dimensional solubility parameters" J. Paint Technol. 39, 105 (1967). Specifically:

dD characterizes the London dispersion forces derived from the formation of dipoles induced during molecular impacts;

dP characterizes the Debye forces of interaction between permanent dipoles;

dH characterizes the specific forces of interaction (of the type: hydrogen bonding, acid/base, donor/acceptor, etc.);

dA is determined by the equation:

$$dA = (d^{P^2} + dH^2)^{1/2}$$

The parameters dD, dP, dH and dA are expressed in $(J/cm^3)^{1/2}$.

According to the present invention, the oily phase preferably comprises at least one oil such that $15.5 \leq dD \leq 18.0$ and $0 \leq dA \leq 6.5$. The parameters dD and dA more preferably satisfy the condition: $16.0 \leq dD \leq 18.0$ and $0 \leq dA \leq 5.5$.

Among the oils satisfying the inequalities $15.5 \leq dD \leq 18.0$ and $0 \leq dA \leq 6.5$, those which may preferably by mentioned, for example, as:

mineral oils such as liquid paraffin and liquid petrolatum;

oils of animal origin such as perhydrosqualene;

oils of plant origin such as jojoba oil, sesame oil, rapeseed oil, karite butter and the liquid fraction thereof; and synthetic oils such as fatty esters, for instance purcellin oil, 2-ethylhexyl palmitate, 2-octyldodecyl stearate, 2-octyldodecyl erucate, isosteryl isostearate, 2-octyldodecyl benzoate and hydrogenated isoparaffin (6–8 mol of isobutylene).

The oily phase of the compositions according to the invention may also contain other types of oils which do not satisfy the conditions of Hansen's solubility parameters determined above, such as, for example, triglycerides of caprylic/capric acids, octyldodecanol, and isohexadecane.

These other oils, if present, are preferably present in the oily phase at concentrations of less than or equal to 15% by weight relative to the total weight of the oily phase. The oily phase thus preferably comprises from 85 to 100% of oil corresponding to the conditions relating to parameters dD and dA defined above.

The crosslinked homopolymers or copolymers used in the compositions according to the invention preferably comprise at least one cationic or anionic monomer containing ethylenic unsaturation and a crosslinking agent containing polyethylenic unsaturation.

The anionic monomer is preferably chosen from (meth) acrylic acid, ammonium (meth)acrylate and 2-acrylamido-2-methylpropanesulphonic acid, as well as their salts.

The cationic monomer is preferably chosen from dialkylaminoalkyl (meth)acrylates, more preferably dimethylaminoethyl methacrylate, and from dialkylaminoalkyhl(meth) acrylamides and quaternary salts or acids thereof, the alkyl radicals preferably being $C_1$–$C_4$.

The crosslinked copolymers according to the invention preferably comprise a nonionic comonomer chosen from methacrylamide, acylamide and $C_{10}$–$C_{30}$ esters of (meth) acrylic acid.

The crosslinking agents containing polyethylenic unsaturation are preferably chosen from divinylbenzene; tetraallyloxyethane; diallyl ether; polyallyl polyglyceryl ethers; allyl ethers of alcohols from the sugar series such as erythritol, pentaerythritol, arabitol, sorbitol or glucose; methylenebis(acrylamide); ethylene glycol di-(methyl) acrylate; di-(meth)acrylamide; cyanomethyl acrylate; vinyloxyethyl (meth)acrylate and metal salts of any of these compounds.

The sugars included in the sugar series, as referred to in the preceding paragraph, preferably comprise sugars containing 5 or 6 carbon atoms, including monosaccharides such as fructose, glucose, galactose, xylose, mannose, lyxose, arabinose, and mixtures of these, and oligosaccharides such as maltose, xylobiose, isomallose, cellobiose, gentiobiose, lactose, sucrose, nigerose, turanose, faffinose, gentianose, melezitose, and mixtures of these.

The crosslinked homopolymers or copolymers in accordance with the invention are preferably chosen from:

(a) acrylic acid homopolymers crosslinked with an allyl ether of an alcohol from the sugar series, such as the products sold under the names CARBOPOLS 980, 981, 954, 2984 and 5984 by the company Goodrich or the products sold under the names SYNTHALEN M and SYNTHALEN K by the company 3 VSA;

(b) copolymers of 2-acrylamido-2-methylpropanesulphonic acid which is partially or totally neutralized (with a base such as sodium hydroxide, potassium hydroxide or an amine) and of acrylamide, such as the product described in Example 1 of European patent application EP-A-503,853;

(c) ammonium acrylate homopolymers such as the product sold under the name MICROSAP PAS 5193 by the company Hoechst, or copolymers of ammonium acrylate and of acrylamide, such as the product sold under the name BOZEPOL C NOUVEAU, or the product PAS 5193 sold by the company Hoechst (which are described and prepared in French patent No. FR 2,416, 723, and U.S. Pat. Nos. 2,798,053 and 2,923,692, the disclosures of which are incorporated by reference);

(d) crosslinked homopolymers of dimethylaminoethyl methacrylate quaternized with methyl chloride, such as the products sold under the names SALCARE 95 and SALCARE 96 by the company Allied Colloids, or the copolymers of dimethylaminoethyl methacrylate which is quaternized with methyl chloride and of acrylamide, such as the product SALCARE SC92 sold by Allied Colloids, or the product PAS 5194 sold by Hoechst (which are described and prepared in European patent application EP-A-395,282, the disclosure of which is incorporated by reference).

The crosslinked homopolymers or copolymers are present in the compositions of the invention at active material concentrations preferably ranging from 0.2 to 10% by weight, in particular from 0.8 to 8% by weight, and more particularly from 0.2 to 5% by weight, relative to the total weight of the composition.

The composition according to the invention may also contain emulsifying nonionic surfactants such as oxyethylenated alkylphenols, such as the product sold under the name NIKKOLI HCO (oxyethylenated hydrogenated ricinoleic triglycerides (60 EO)) by the company Nikkol, or the product sold under the name SOLUBILISANT LRI (oxyethylenated butyl alcohol (26 EO)) with a mixture of oxyethylenated hydrogenated castor oil (40 EO) and water (54/36) by the company Wacker. They are preferably present at concentrations ranging from 0.1 to 2% by weight and more preferably from 0.5 to 1.5% by weight.

The compositions in accordance with the invention may also contain thickening agents which have a low flow threshold, namely agents which can flow under their own weight and which have a low gelling power. Examples which may be mentioned are natural gelling agents such as galactomannans, for instance guar and carob; carrageenans such as D-galactopyranose (product AUBYGUM X2 sold by the company Sanofi); sodium alginates (polymannuronate and guluronate); cellulose and derivatives thereof such as methylcellulose, propylcellulose, hydroxypropylmethylcellulose; xanthan gums such as those consisting of D-glucose, D-mannose and D-glucuronic acid; fucose-rich polysaccharides such as the product FUCOGEL 1000 sold by the company Solabia.

The compositions according to the invention may also contain from synergists such as alkanolamides, for instance monoethanolamides and dialkanolamides; and more particularly monoisopropanolamides and diethanolamides; alkylamidodimethylamines; amine oxide derivatives such as alkyldimethylamine oxides, alkyldihydroxyethylamine oxides, alkylamidomethylamine oxides, alkylamidohydroxyethylamine oxides and alkylamidohydroxyethylamine oxides. They are preferably present in concentrations of less than or equal to 10% by weight relative to the total weight of the composition.

The compositions in accordance with the invention may also contain, in the oily phase, one or more lipophilic cosmetic and/or dermatological active agents such as, for example, anti-free-radical agents, ceramides, lipophilic formulation additives such as preserving agents, antioxidants and perfumed oils.

The compositions according to the invention may also contain, in the aqueous medium, hydrophilic cosmetic and/ or dermatological active agents which are commonly used, such as polyols, for instance glycerol, 2,4,4'-trichloro-2'-hydroxydiphenyl ether, the monoethanolamine salt of 1-hydroxy-4-methyl-6-trimethylpentyl-2-pyridone (or piroctone olamine) such as the product OCTOPIROX sold by the company Hoechst, alpha-hydroxy acids, keratolytic agents such as urea, salicylic acid and derivatives thereof such as 5-n-octanoylsalicylic acid, antibacterial agents, antiseborrhoeic agents and antidandruff agents. The compositions according to the invention may contain standard formulation additives such as pigments, pearlescent agents, inorganic or organic fillers such as talc, kaolin, silica powder or polyethylene powder, and expanded thermoplastic hollow particles such as the product EXPANCEL 550 DE 20 sold by the company Nobel Casco.

The compositions according to the invention preferably have a viscosity ranging from 1.5 to 6 Pa s and more preferably ranging from 2.5 to 4 Pa s.

The compositions according to the invention, i.e., in cream form, produce sufficiently abundant foam on contact with water.

Another subject of the invention is of a cosmetic or dermatological composition for cleansing the skin, the mucous membranes, the hair or the scalp, comprising a foaming cream as defined above.

The foaming creams of the invention may be used as bases for products for the cleansing of/removal of make-up from the skin, the eyes and/or the face.

The foaming creams of the invention may also be used as bases for cleansing and care products for the hair or the scalp, such as two-in-one shampoos.

The foaming creams of the invention may also be used as bases for hygiene and care products for the skin and/or the body, such as two-in-one shower creams.

Another subject of the invention is directed to a process for cleansing the skin, the mucous membranes, the hair or the scalp, which comprises applying in the presence of water, to the skin, the mucous membranes, the hair or the scalp, a cosmetically effective amount of an oil-in-water emulsion as described above to obtain a foam; and removing, by rinsing with water, any foam or dirt residues from the skin, mucous membranes, hair or scalp.

Obviously, a person skilled in the art will take care to select the possible additional compound or compounds and/or the amounts thereof such that the advantageous properties intrinsically associated with the ternary combination in accordance with the invention are not damaged, or are not substantially damaged, by the addition or additions envisaged.

The examples which follow are intended to illustrate the invention without, however, limiting the scope thereof.

EXAMPLES

In all the examples of foaming creams which follow, the amount of foam produced was measured according to the following method:

2.5 g of test composition diluted in 50 ml of water were placed in a tall 400 ml beaker.

A foam was formed by stirring the composition in solution for 6 minutes at 1320 rev/minute using a Turbotest 10-14 Rayneri machine equipped with a centripetal rod of diameters 30–40–55 cm; the latter was placed off-center to the left in the beaker.

The product obtained was then transferred into a 500 ml measuring cylinder with an error of 2.5 ml.

The volume of the product obtained (foam) was measured at time intervals of t=0, t=3 minutes, and t=5 minutes.

If a foam volume of less than 150 ml or decomposition of the foam after standing for a few minutes was obtained with the test composition by this method for measuring the volume of the foam, the foaming properties of the test composition were considered to be mediocre and unusable for cosmetic, dermatological or hygienic use.

Examples 1 to 7

| EXAMPLES | 1 | 2 | 3 | 4 | 5 | 6 | 7 |
|---|---|---|---|---|---|---|---|
| GELLING AGENTS: | | | | | | | |
| Carbopol 980° | 0.9 g | 0.9 g | 1.1 g | — | 0.9 g | — | — |
| Synthalon K.° | — | — | — | — | — | 1 g | — |
| PAS 5183° | — | — | — | — | — | — | 6 g |
| Salcare SC 95° | — | — | — | 4 g | — | — | — |
| Gelling agent(s) additives | | | | | | | |
| Aubigum X2° | — | — | 0.1 g | — | — | — | — |
| NONIONIC SURFACTANTS: | | | | | | | |
| Chimazane Nf° | 5 g | 5 g | 5 g | 5 g | 5 g | 5 g | 5 g |
| Surfactant of formula (I) | — | — | — | — | — | — | 2 g |
| SLM SPG 120° | — | — | — | — | 1 g | — | — |
| Nikkol MCO-60° | | | | | | | |
| FILLERS: | | | | | | | |
| Expancol 551 DE 20° | — | — | — | 0.75 g | — | — | — |
| OIL(S): | | | | | | | |
| Liquid petrolatum | — | — | — | — | 50 g | — | — |
| Liquid fraction of kante butter | — | — | 20 g | — | — | — | — |
| Sesame oil | 25 g | — | — | 25 g | — | — | 5 g |
| Rapeseed oil | — | 25 g | — | — | — | 10 g | — |
| Triglycerides of capylric/capric acids | — | — | 3 g | — | — | — | — |
| ACTIVE AGENTS | | | | | | | |
| Piroctone alamine | 0.2 g | — | 0.2 g | — | — | — | — |
| Lactic acid | — | — | — | — | — | — | 0.2 g |
| 5-n-Octanoylsallcylic acid | — | — | 0.2 g | — | — | — | — |
| Sodium hydroxide | 0.18 g | 0.18 g | 0.18 g | — | 0.18 g | 0.18 g | — |
| Glycerol | 6 g | 6 g | 6 g | 6 g | 6 g | — | 3 g |

-continued

| EXAMPLES | 1 | 2 | 3 | 4 | 5 | 6 | 7 |
|---|---|---|---|---|---|---|---|
| Water qs | 100 g | 100 g | 100 g | 100 g | 100 g | 100 g | 100 g |
| Preserving agent(s) qs | | | | | | | |
| Antioxidant(s) qs | | | | | | | |
| Volume of foam (ml) | 255 | 240 | 200 | 260 | 210 | 255 | 265 |

Each of the compositions of Examples 1 to 7 had satisfactory foaming properties.

Examples 8 to 14

| EXAMPLES | 8 | 9 | 10 | 11 | 12 | 13 | 14 |
|---|---|---|---|---|---|---|---|
| GELLING AGENTS: | | | | | | | |
| Carbopol 980° | 0.9 g | 0.9 g | 11 g | — | 0.9 g | — | — |
| Synthalon K.° | — | — | — | — | — | 1 g | — |
| PAS 5183° | — | — | — | — | — | — | 5 g |
| Salcare SC 95° | — | — | — | 4 g | — | — | — |
| Gelling agent(s) additives | | | | | | | |
| Aubigum X2° | — | — | 0.1 g | — | — | — | — |
| NONIONIC SURFACTANTS: | | | | | | | |
| Plantaren 2000° | 10 g | 10 g | 10 g | 10 g | 10 g | 10 g | 10 g |
| Surfactant of formula (II) | | | | | | | |
| SLM SPG 120° | — | — | — | — | — | — | 2 g |
| Nikkol MCO-60° | — | — | — | — | 1 g | — | — |
| FILLERS: | | | | | | | |
| Expancol 551 DE 20° | — | — | — | 0.75 g | — | — | — |
| OIL(S): | | | | | | | |
| Liquid fraction of kante butter | 25 g | — | — | 25 g | 50 g | — | 5 g |
| Sesame oil | — | — | 20 g | — | — | — | — |
| Rapeseed oil | — | 25 g | — | — | — | 10 g | — |
| Triglycerides of capylric/capric acids | — | — | 3 g | — | — | — | — |
| ACTIVE AGENTS | | | | | | | |
| Piroctone alamine | 0.2 g | — | 0.2 g | — | — | — | 0.2 g |
| Lactic acid | — | — | — | — | — | — | — |
| 5-n-Octanoylsallcylic acid | — | — | 0.2 g | — | — | — | — |
| Sodium hydroxide | 0.18 g | 0.18 g | 0.18 g | — | 0.18 g | 0.18 g | — |
| Glycerol | 6 g | 6 g | 6 g | 6 g | 6 g | — | 3 g |
| Water qs | 100 g | 100 g | 100 g | 100 g | 100 g | 100 g | 100 g |
| Preserving agent(s) qs | | | | | | | |
| Antioxidant(s) qs | | | | | | | |
| Volume of foam (ml) | 255 | 240 | 200 | 260 | 210 | 255 | 265 |

(*) starting material containing 50% active material

Each of the compositions of Examples 8 to 14 had satisfactory foaming properties.

Comparative Examples

The amount of the foam obtained from different creams containing different oils and having different values of Hansen solubility parameters dA and dD were studied. The compositions of the invention containing, as the oily phase, an oil satisfying the relationships $15.5 \leq dD \leq 18$ and $0 \leq dA \leq 6.5$, was compared with compositions containing, as the oily phase, an oil which did not satisfy these conditions. The volume of foam was measured according to the method defined above.

The test compositions had the formulation:

| | |
|---|---|
| nonionic surfactant of formula (I) CHIMEXANE NF | 5.0 g |
| oil of dA, dD parameters | 25.0 g |
| crosslinked acrylic homopolymer gelling agent CARBOPOL 980 | 0.9 g |
| water qs | 100.0 g |

The oils used were:

isohexadecane 2-ethylhexyl palmitate 2-octyldodecyl stearate 2-octyldodecyl erucate isostearyl isostearate 2-octyldodecyl benzoate
jojoba oil
sesame oil
triglycerides of capric/caprylic acids
octyldodecanol.

The results are summarized in the following table:

| Oil used in the test composition | dD (J/cm$^3$) ® | dA (J/cm$^3$) ® | Volume of foam (ml) |
|---|---|---|---|
| Isohexadecane | 15.32 | 0 | 105 |
| 2-Octyldodecyl erucate | 16.36 | 3.21 | 265 |
| Jojoba oil | 16.33 | 3.33 | 265 |
| 2-Octyldodecyl stearate | 16.40 | 3.37 | 260 |
| Isostearyl isostearate | 16.31 | 3.46 | 245 |
| 2-Octyldodecyl benzoate | 17.08 | 4.21 | 220 |
| 2-Ethylhexyl palmitate | 16.20 | 4.23 | 190 |
| Sesame oil | 16.36 | 4.85 | 260 |
| Triglycerides of capric/caprylic acids | 16.64 | 6.69 | 70 |
| Octyldodecanol. | 16.36 | 7.69 | 65 |

The results obtained show that the phases consisting of oils not corresponding to the conditions determined on the Hansen solubility parameters, namely $15.5 \leq dD \leq 18$ and $0 \leq dA \leq 6.5$, do not make it possible to obtain creams having satisfactory foaming properties; this is the case for isohexandecane, triglycerides of capric/caprylic acids and octyldodecanol.

What is claimed is:

1. A foaming oil-in-water emulsion in the form of a cream, which comprises, in a cosmetically acceptable aqueous medium, at least:
    a) from 5 to 20% by weight, relative to the total weight of the composition, of a nonionic surfactant system consisting of at least one foaming nonionic surfactant and at least one emulsifying nonionic surfactant,
    wherein said at least one foaming nonionic surfactant is selected from:
       i) the compounds of formula (I):

(I)

in which:
R represents an aliphatic, cycloaliphatic or arylaliphatic radical or a mixture of radicals having from 7 to 21 carbon atoms, wherein the aliphatic chains are saturated or unsaturated, linear or branched, and may contain sulphur or oxygen atoms; and
n represents any integer or fraction greater than 1 and less than or equal to 10 and denotes the degree of polymerization;
       ii) the compounds of formula (II)

$R^1O(G)_p$ in which $R^1$ is a monovalent hydrocarbon chain containing from 1 to 30 carbon atoms, G is a saccharide containing from 5 to 6 carbon atoms and p is a statistical average value ranging from 1 to 6;
       iii) polydimethylsiloxanes containing glucoside groups and polydimethylsiloxanes containing alkylphosphobetaine groups; and
       iv) mixtures of the above compounds;
    and wherein said at least one emulsifying nonionic surfactant is present in an amount up to 2% by weight and is selected from oxyethylenated alkylphenols;
    b) from 10 to 50% by weight, relative to the total weight of the composition, of an oily phase comprising from 85 to 100% by weight of at least one water-insoluble oil, wherein said at least one water-insoluble oil has solubility parameters dD, dP and dH according to Hansen's solubility space which satisfy the conditions:

$15.5 \ (J/cm^3)^{1/2} \leq dD \leq 18.0 \ (J/cm^3)^{1/2}$ and $0 \ (J/cm^3)^{1/2} \leq dA \leq 6.5 \ (J/cm^3)^{1/2}$ with

$dA=(dP^2+dH^2)^{1/2};$ and
    c) as a gelling agent, at least one crosslinked homopolymer or copolymer formed from at least one cationic or anionic monomer containing ethylenic unsaturation and from a crosslinking agent containing polyethylenic unsaturation; wherein said copolymer does not comprise copolymers containing a majority fraction of at least one olefinically unsaturated $C_3$–$C_6$ acid and a minority fraction of at least one ester of an olefinically unsaturated $C_3$–$C_6$ acid with a $C_{10}$–$C_{30}$ alcohol.

2. An emulsion according to claim 1, which comprises:
    a) from 5 to 10% by weight, relative to the total weight of the composition, of an exclusively nonionic surfactant system comprising at least one foaming nonionic surfactant; and
    b) from 10 to 30% by weight, relative to the total weight of the composition, of an oily phase comprising at least one water-insoluble oil whose solubility parameters according to Hansen's solubility space are as defined in claim 1.

3. An emulsion according to claim 1, wherein said at least one foaming nonionic surfactant has a foaming power determined by a foam height of more than 100 mm according to the Ross-Miles method for a 0.1% by weight solution in distilled water at 25° C.

4. An emulsion according to claim 1, wherein said compounds of formula (1) are selected from those in which R represents a $C_9$–$C_{12}$ alkyl radical or a mixture of radicals and n represents a statistical value ranging from 3 to 4.

5. An emulsion according to claim 1, wherein said at least one water-insoluble oil is selected from mineral oils, oils of animal origin and synthetic oils.

6. An emulsion according to claim 5, wherein said at least one water-insoluble oil is selected from liquid paraffin, liquid petrolatum, perhydrosqualene, jojoba oil, sesame oil, rapeseed oil, karite butter, the liquid fraction of karite butter, purcellin oil, 2-ethylhexyl palmitate, 2-octyldodecyl stearate, 2-octyldodecyl erucate, isostearyl isostearate and 2-octyldodecyl benzoate and hydrogenated isoparaffin (6.8 mol of isobutylene).

7. An emulsion according to claim 1, which further comprises at least one water-insoluble oil whose solubility parameters dA and dD satisfy the conditions:

$$16.0 \ (J/cm^3)^{1/2} \leq dD \leq 18.0 \ (J/cm^3)^{1/2}$$

and $$0 \ (J/cm^3)^{1/2} \leq dA \leq 5.5 \ (J/cm^3)^{1/2}.$$

8. An emulsion according to claim 1, wherein said gelling agent comprises a crosslinked homopolymer or copolymer formed from at least one anionic monomer selected from (meth)acrylic acid, ammonium (meth)acrylate, 2-acrylamido-2-methylpropanesulphonic acid and the salts of said compounds.

9. An emulsion according to claim 1, wherein said gelling agent comprises a crosslinked homopolymer or copolymer formed from at least one cationic monomer selected from dialkylaminoalkyl (meth)acrylates, dialkylaminoalkyl (meth)acrylamides and the quaternary salts and acids or said compounds.

10. An emulsion according to claim 1, wherein said crosslinking agent containing polyethylenic unsaturation is selected from divinylbenzene, tetraallyloxyethane, diallyl ether, polyallyl polyglyceryl ethers, allyl polyglyceryl ethers, allyl ethers of alcohols from the sugar series, methylenebis(acrylamide), ethylene glycol di-methacrylate, di-(meth)acrylamide, cyanomethyl acrylate, vinyloxyethyl (meth)acrylate and the metal salts of said compounds.

11. An emulsion according to claim 8, wherein said crosslinked homopolymer or copolymer is further formed from a nonionic comonomer selected from acrylamide, methacrylamide and $C_{10}$–$C_{30}$ esters of (meth)acrylic acid.

12. An emulsion according to claim 1, wherein said gelling agent is selected from:
(a) acrylic acid homopolymers crosslinked with an allyl ether of an alcohol from the sugar series;
(b) crosslinked copolymers of 2-acrylamido-2-methylpropanesulphonic acid which is partially or totally neutralized and of acrylamide;
(c) crosslinked homopolymers of ammonium acrylate or crosslinked copolymers of ammonium acrylate and of acrylamide; and
(d) crosslinked homopolymers of dimethylaminoethyl methacrylate quaternized with methyl chloride or the copolymers of this same monomer with acrylamide.

13. An emulsion according to claim 1, wherein said gelling agent is present in active material concentrations ranging from 0.8 to 8% by weight relative to the total weight of said emulsion.

14. An emulsion according to claim 1, which further comprises at least one emulsifying nonionic surfactant, said at least one emulsifying nonionic surfactant being different from said at least one foaming nonionic surfactant.

15. An emulsion according to claim 1, which further comprises at least one thickening agent.

16. An emulsion according to claim 15, wherein said at least one thickening agent is selected from galactomannans, carrageenans, sodium alginates, cellulose and derivatives thereof, xanthan gums, and fucose-rich polysaccharides.

17. An emulsion according to claim 1, which further comprises at least one foam synergist.

18. An emulsion according to claim 17, wherein said at least one foam synergist is selected from alkanolamides, alkylamidodimethylamines and amine oxide derivatives.

19. An emulsion according to claim 1, which further comprises at least one additive selected from lipophilic or hydrophilic cosmetic or dermatological active agent, antioxidant, preserving agent, fragrance, antibacterial agent, antiseborrhoreic agent, antidandruff agent, pigment, keratolytic agent, dye, pearlescent agent, inorganic filler and organic filler.

20. An emulsion according to claim 1, which has a viscosity ranging from 2.5 to 6 Pa s.

21. An emulsion according to claim 20, which has a viscosity ranging from 2.5 to 4 Pa.

22. A process for cleansing the skin, the mucous membranes, the hair, or the scalp, which comprises:
applying, in the presence of water, to the skin, the mucous membranes, the hair or the scalp, a cosmetically effective amount of an oil-in-water emulsion according to claim 1 to obtain a foam; and
removing, by rinsing with water, any foam or dirt residues from said skin, mucous membranes, hair or scalp.

23. A cosmetic or dermatological composition for cleansing the skin, the mucous membranes, the hair or the scalp, which comprises an effective amount of a foaming oil-in-water emulsion in the form of a cream, which emulsion comprises, in a cosmetically acceptable aqueous medium, at least:
from 5 to 20% by weight, relative to the total weight of the composition, of a nonionic surfactant system consisting of at least one foaming nonionic surfactant and at least one emulsifying nonionic surfactant:
wherein said at least one foaming nonionic surfactant is selected from:
i) the compounds of formula (I):

(I)

in which:
R represents an aliphatic, cycloaliphatic or arylaliphatic radical or a mixture of radicals having from 7 to 21 carbon atoms, wherein the aliphatic chains are saturated or unsaturated, linear or branched, and may contain sulphur or oxygen atoms; and
n represents any integer or fraction greater than 1 and less than or equal to 10 and denotes the degree of polymerization;
ii) the compounds of formula (II)

in which $R^1$ is a monovalent hydrocarbon chain containing from 1 to 30 carbon atoms, G is a saccharide containing from 5 to 6 carbon atoms and p is a statistical average value ranging from 1 to 6;
iii) polydimethylsiloxanes containing glucoside groups and polydimethylsiloxanes containing alkylphosphobetaine groups; and
iv) mixtures of the above compounds;
and wherein said at least one emulsifying nonionic surfactant is present in an amount up to 2% weight and is selected from oxyethylenated alkylphenols;
b) from 10 to 50% by weight, relative to the total weight of the composition, of an oily phase comprising from 85 to 100% by weight of at least one water-insoluble oil, wherein said at least one water-insoluble oil has solubility parameters dD, dP and dH according to Hansen's solubility space which satisfy the conditions:

$$15.5\ (J/cm^3)^{1/2} \leq dD \leq 18.0\ (J/cm^3)^{1/2}$$

and $$0\ (J/cm^3)^{1/2} \leq dA \leq 6.5\ (J/cm^3)^{1/2}$$

with $$dA=(dP^2+dH^2)^{1/2};$$

and c) as a gelling agent, at least one crosslinked homopolymer or copolymer formed from at least one cationic or anionic monomer containing ethylenic unsaturation and from a crosslinking agent containing polyethylenic unsaturation; wherein said copolymer does not comprise copolymers containing a majority fraction of at least one olefinically unsaturated $C_3$–$C_6$ acid and a minority fraction of at least one ester of an olefinically unsaturated $C_3$–$C_6$ acid with a $C_{10}$–$C_{30}$ alcohol.

24. A process for cleansing and/or caring for the skin, for removing make-up from the skin, the eyes and the face, and/or for cleansing and caring for the hair, which comprises applying thereto a cosmetically effective amount of a foaming oil-in-water emulsion as a case, which emulsion is in the form of a cream and, which comprises, in an cosmetically acceptable aqueous medium, at least:

a) from 5 to 20% by weight, relative to the total weight of the composition, of a nonionic surfactant system consisting of at least one foaming nonionic surfactant and at least one emulsifying nonionic surfactant;

wherein said at least one foaming nonionic surfactant is selected from:

i) the compounds of formula (I):

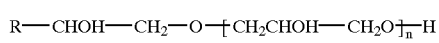

(I)

in which:

R represents an aliphatic, cycloaliphatic or arylaliphatic radical or a mixture of radicals having from 7 to 21 carbon atoms, wherein the aliphatic chains are saturated or unsaturated, linear or branched, and my contain sulfur or oxygen atoms; and n represents any integer or fraction greater than 1 and less than or equal to 10 and denotes the degree of polymerization;

ii) the compounds of formula (II)

$$R^1O(G)_p$$

in which $R^1$ is a monovalent hydrocarbon chain containing from 1 to 30 carbon atoms, G is a saccharide containing from 5 to 6 carbon atoms and p is a statistical average value ranging from 1 to 6;

iii) polydimethylsiloxanes containing glucoside groups and polydimethylsiloxanes containing alkylphosphobetaine groups; and iv) mixtures of the above compounds;

and wherein said at least one emulsifying nonionic surfactant is present in an amount up to 2% by weight and is selected from oxyethylenated alkylphenols;

b) from 10 to 50% by weight, relative to the total weight of the composition, of an oily phase comprising from 85 to 100% by weight of at least one water-insoluble oil, wherein said at least one water-insoluble oil has solubility parameters dD, dP and dH according to Hansen's solubility space which satisfy the conditions:

$$15.5\ (J/cm^3)^{1/2} \leq dD \leq 18.0\ (J/cm^3)^{1/2}$$

and $$0\ (J/cm^3)^{1/2} \leq dA \leq 6.5\ (J/cm^3)^{1/2}$$

with $$dA=(dP^2+dH^2)^{1/2};$$

and c) as a gelling agent, at least one crosslinked homopolymer or copolymer formed from at least one cationic or anionic monomer containing ethylenic unsaturation and from a crosslinking agent containing polyethylenic unsaturation; wherein said copolymer does not comprise copolymers containing a majority fraction of at least one olefinically unsaturated $C_3$–$C_6$ acid and a minority fraction of at least one ester of an olefinically unsaturated $C_3$–$C_6$ acid with a $C_{10}$–$C_{30}$ alcohol.

* * * * *

UNITED STATES PATENT AND TRADEMARK OFFICE
CERTIFICATE OF CORRECTION

PATENT NO.   : 6,579,907 B1
DATED        : June 17, 2003
INVENTOR(S)  : Laurence Sebillotte-Arnaud et al.

It is certified that error appears in the above-identified patent and that said Letters Patent is hereby corrected as shown below:

Title page,
Item [57], ABSTRACT,
Line 1, "A forming" should read -- A foaming --.

Column 14,
Line 25, insert "a)" before "from 5 to 20% by weight".

Column 15,
Line 27, "case" should read -- base --.
Line 28, "in an" should read -- in a --.

Signed and Sealed this

Twenty-eighth Day of October, 2003

JAMES E. ROGAN
*Director of the United States Patent and Trademark Office*